United States Patent
Dhariya

(10) Patent No.: US 12,076,766 B2
(45) Date of Patent: Sep. 3, 2024

(54) SMART PORTABLE DEVICE AND SYSTEM FOR DISPOSAL OF SANITARY WASTE

(71) Applicant: PADCARE LABS PRIVATE LIMITED, Maharashtra (IN)

(72) Inventor: Ajinkya Dhariya, Maharashtra (IN)

(73) Assignee: PADCARE LABS PRIVATE LIMITED, Maharashtra (IN)

( * ) Notice: Subject to any disclaimer, the term of this patent is extended or adjusted under 35 U.S.C. 154(b) by 389 days.

(21) Appl. No.: 17/617,977

(22) PCT Filed: Jun. 9, 2020

(86) PCT No.: PCT/IN2020/050509
§ 371 (c)(1),
(2) Date: Dec. 10, 2021

(87) PCT Pub. No.: WO2020/250239
PCT Pub. Date: Dec. 17, 2020

(65) Prior Publication Data
US 2022/0250127 A1    Aug. 11, 2022

(30) Foreign Application Priority Data
Jun. 13, 2019  (IN) .............................. 201921023476

(51) Int. Cl.
*B02C 19/18* (2006.01)
*A01N 25/04* (2006.01)
(Continued)

(52) U.S. Cl.
CPC ................ *B09B 3/35* (2022.01); *A01N 25/04* (2013.01); *A61F 13/84* (2013.01); *A61L 2/10* (2013.01);
(Continued)

(58) Field of Classification Search
CPC ......... B02C 23/18; B02C 23/08; B02C 23/10; B02C 18/142; B02C 18/148; B02C 18/086; B02C 19/18
See application file for complete search history.

(56) References Cited

U.S. PATENT DOCUMENTS 2,753,121 A * 7/1956 Elfenbein ............... B02C 25/00
241/38
5,152,467 A * 10/1992 Hwang ..................... B02C 7/08
241/DIG. 38
(Continued)

FOREIGN PATENT DOCUMENTS

| CN | 106861853 A | * | 6/2017 | ........... B02C 18/145 |
| CN | 114100802 A | * | 3/2022 | ........... B02C 18/142 |

(Continued)

OTHER PUBLICATIONS

Corresponding International Patent Application No. PCT/IN2020/050509, International Search Report mailed Sep. 14, 2020.
(Continued)

*Primary Examiner* — Faye Francis
(74) *Attorney, Agent, or Firm* — Cooper Legal Group, LLC

(57) ABSTRACT

A hygienic disposal device for sanitary waste includes a supporting structure frame for mounting one or more components, including an opening lid hingedly connected to a hopper equipped with spray nozzles for disinfectant solution and water spraying. A shredder is connected to the hopper for shredding the waste, followed by a mixing chamber for homogenously mixing shredded waste with water. Valves at the bottom of the mixing chamber separate cellulose and plastic waste. Two rotating drums dewater and dry the separated waste, while a dryer blows hot air for further drying. An outlet discharges separated water into municipal sewage lines.

10 Claims, 4 Drawing Sheets

(51) Int. Cl.
  *A61F 13/84* (2006.01)
  *A61L 2/10* (2006.01)
  *A61L 2/22* (2006.01)
  *A61L 2/26* (2006.01)
  *A61L 11/00* (2006.01)
  *B09B 3/35* (2022.01)
  *B09B 3/38* (2022.01)
  *B09B 3/50* (2022.01)
  *B09B 3/70* (2022.01)
  *B29B 17/02* (2006.01)
  *B29B 17/04* (2006.01)
  *B09B 101/67* (2022.01)
  *B29L 31/48* (2006.01)

(52) U.S. Cl.
  CPC .................. *A61L 2/22* (2013.01); *A61L 2/26* (2013.01); *A61L 11/00* (2013.01); *B09B 3/38* (2022.01); *B09B 3/50* (2022.01); *B09B 3/70* (2022.01); *B29B 17/02* (2013.01); *B29B 17/0412* (2013.01); *A61F 2013/8402* (2013.01); *A61L 2202/11* (2013.01); *A61L 2202/14* (2013.01); *A61L 2202/15* (2013.01); *B09B 2101/67* (2022.01); *B29B 2017/0224* (2013.01); *B29L 2031/4878* (2013.01)

(56) References Cited

U.S. PATENT DOCUMENTS

| | | | | |
|---|---|---|---|---|
| 5,354,000 | A * | 10/1994 | Wright | A61L 11/00 241/606 |
| 5,429,311 | A * | 7/1995 | Cina | D21B 1/026 241/38 |
| 5,618,003 | A | 4/1997 | Akiyoshi et al. | |
| 6,827,302 | B2 | 12/2004 | Hohnen et al. | |
| 7,726,593 | B2 * | 6/2010 | Heidel | B03B 9/061 241/29 |
| 2013/0037635 | A1 * | 2/2013 | Singh | D21C 9/007 241/3 |
| 2016/0001296 | A1 * | 1/2016 | Scaife | B02C 13/2804 241/24.1 |
| 2016/0288996 | A1 * | 10/2016 | Arsovic | B65F 1/14 |
| 2020/0406268 | A1 * | 12/2020 | Hall | C02F 11/122 |

FOREIGN PATENT DOCUMENTS

| | | | | |
|---|---|---|---|---|
| JP | 2019085686 | A * | 6/2019 | ............. A61F 13/15 |
| WO | WO-2007091674 | A1 * | 8/2007 | ......... B02C 18/0084 |
| WO | WO-2017055875 | A1 * | 4/2017 | ............. A61L 11/00 |
| WO | 2018102898 | A1 | 6/2018 | |
| WO | WO-2020040140 | A1 * | 2/2020 | ............ B01F 15/068 |

OTHER PUBLICATIONS

Corresponding International Patent Application No. PCT/IN2020/050509, Written Opinion of the International Searching Authority mailed Sep. 14, 2020.

Corresponding India Patent Application No. 201921023476, Office Action dated Nov. 25, 2020. English Translation.

* cited by examiner

SMART PORTABLE DEVICE AND SYSTEM FOR DISPOSAL OF SANITARY WASTE

FIELD OF INVENTION

The present invention relates generally to the field of waste management, disinfection, and disposal.

More specifically the present invention relates to low cost, simple, portable, instant and environment friendly sanitary waste disposal device and system.

Still more particularly the present invention relates to a system and device for disinfection and disposal of used/soiled sanitary pads or napkins, feminine hygiene products and diapers etc.

BACKGROUND OF INVENTION

In India about 12 billion sanitary napkins get generated every year and more than 80% of the sanitary waste is either getting flushed down to the toilet or getting dumped in the landfill or water bodies. The plastic used in sanitary napkins, which is non-biodegradable, is not only harmful for health, but also has negative consequences on the environment by staying in the landfills. These practices lead to harmful environmental consequences, as well as entail long term economic burden on country in the forms of health costs, pollution etc. Interlinked causes explain this problem—Environment hazard, health cost and the lack of suitable products available in the market. This soiled waste is primary way for transmission of viruses like HIV, HBV along with pathogens. In India there are 1 million cases every year for HIV-HBV infection and 60% Indian women facing infection of urinary tract having one of the reason bad menstrual disposal facilities.

The disposal of sanitary napkins, though more a health and hygiene issue, gets complicated when the waste is thrown away polluting the environment with its non-biodegradable content and inorganic components. These methods lead to adverse impact on the environment and people.

Thus, it would suggest that cost-effective, waste-free options are the most viable solution to waste sanitation issue. One option is use of eco-friendly cloth pads. For an environmental perspective, re-usable cloth is a great alternative to disposable pads. However, it needs proper care in washing and cleaning. Cloth pads has usability question due to bacterial growth on cotton. Also, more water is required for washing and reusing and hence may not be suitable from usability point of view.

Another option for the disposal of sanitary pads is incineration. Incinerators reduce the sanitary waste to sterile ash in a matter of seconds and this can be used as manure or can be flushed down the toilet. However, this method also leads to serious health hazards since it produces harmful gaseous emissions like dioxin and furan in significant amounts. These gases may cause serious health problems such as cancer, immune system damage, reproductive health related dieses etc. The ash produced during incineration process is also a potential health hazard since it contains high concentration of heavy metals like lead, cadmium, copper etc. Other pollutants of concern from incinerators include other halogenated hydrocarbons, acid gases that are precursors of acid rain, particulates responsible for lung infections. Incinerators also had demerits like smell issue, high recurring, and setup cost. Incinerators consumes very high energy. None of the mentioned methods provides recycling of used sanitary napkins.

Hence it is Inevitable to Shift Towards New Kind of Technology that Will Provide Safe, Accessible, and Cost-Effective Sanitary Waste Disposal and Recycling System

OBJECTS OF THE INVENTION

The main object of present invention is to provide safe, instant, low cost, and eco-friendly sanitary waste disposal and recycling solution which overcomes issues of unhygienic environment, smell and unsafe handling.

Another object of present invention is to provide a system for sanitary waste disintegration, disinfection, deodorization, decolorization and deactivation of super absorbent polymer.

Yet another object of present invention is to provide a smart, portable device for sanitary waste disposal and method of disposal thereof.

SUMMARY OF THE INVENTION

The present invention relates to a smart portable device and system for disposal of sanitary waste or disposal of used sanitary pads/Napkins, feminine hygiene products diapers etc. The invention also describes a system for sanitary waste disposal.

In accordance with one aspect of the present invention, features of a smart portable device and system for disposal of sanitary waste effectively and environment friendly to overcome issues of unhygienic environment, bad smell, unsafe handling and reusability, wherein the device comprising an opening lid hingely connected to a hopper with guiding arrangement wherein; said hopper may receive the sanitary waste to be processed and guide used sanitary waste to the next chamber of shredder, said hopper further comprises at least two spray nozzles for spraying the disinfectant solution and water respectively on the soiled sanitary waste pumped from a dilute solution storage and water storage, a shredder fitted to said hopper by a nut and bolt arrangement operably coupled to a controlled motor for shredding the said waste by rotating the shredder blades clockwise as well as anticlockwise for a predetermined time, a mixing chamber arranged at the lower portion of said hopper wherein the shredded sanitary waste incubates for a predetermined period to achieve homogenous mixture by addition of water in order to disinfect the sanitary waste completely, at least two automated valves positioned at the base of said mixing chamber with mesh for one of the valve so as to remove separated cellulose & plastic respectively, at least two rotating drums with a dryer arranged below the said mixing chamber wherein the two automated valves open to receive wet cellulose and wet plastic in two separate rotating drums for dewatering the cellulose waste & plastic waste wherein the water is separated to get a solid mass of plastic and cellulose, said rotating drums wherein the liquid portion is a neutral sewage and directly drain off into municipal sewage line, the dried solid waste is collected in each rotating drum, an outlet means attached to sewage pipeline for discharging neutral liquids into municipal sewage line, are disclosed.

In accordance with another aspect of the present invention, features of a smart portable device and system for disposal of sanitary waste for disposing soiled/used sanitary pads, napkins, diapers and other feminine hygiene products waste effectively and environment friendly, wherein the method of disposal of used/soiled sanitary pads/napkins in environmental friendly way may include but not limited to steps like receiving used sanitary waste, shredding said sanitary waste by a shredder, spraying/mixing the disinfectant solution onto the sanitary waste simultaneously with shredding, treating the disinfected and shredded waste in the mixing chamber for a predetermined time period and separating the liquid content from semisolid waste and throwing out the non hazardous pre-treated liquid into the municipal sewage line, and recycling are disclosed.

In another aspect of the present invention features of a system for disposal of sanitary waste for disposing soiled/used sanitary waste effectively and environment friendly, wherein a system comprising; a plurality of (Secured waste collection bins each for collecting the sanitary waste put by user, a sanitary waste disposal device at centralized location, wherein; each device may comprises an opening lid hingely connected to a hopper with a guiding arrangement wherein; said hopper may receive the sanitary waste to be treated and guide used sanitary waste to the next chamber of shredder, said hopper further comprises at least two spray nozzles for spraying the disinfectant solution on the soiled sanitary waste pumped from a dilute solution storage wherein said solution is stored, a shredder fitted to said hopper by a nut and bolt arrangement operably coupled to a controlled motor for shredding the said waste by rotating the shredder blades clockwise as well as anticlockwise for a predetermined time, a mixing chamber arranged at the lower portion of said hopper wherein the shredded sanitary waste incubates for a predetermined period to achieve homogenous mixture by addition of water in order to disinfect the sanitary waste completely, at least two automated valves positioned at the base of said mixing chamber with mesh so as to remove separated cellulose & plastic respectively, at least two separate rotating drum with a dewatering system wherein the two automated valves open to push wet cellulose waste and wet plastic waste from mixing chamber for drying the cellulose waste & plastic waste wherein the water is separated to get a solid mass of plastic and cellulose, each rotating drum wherein the liquid portion is a neutral sewage and directly drain off into municipal sewage line, the solid waste is collected from an outlet at the lower portion of rotating drum, a display screen for displaying the stage of disposal process carrying out by the device; a microcontroller for controlling the automatic functions of sensors, valves & pump, a data transmission module for transmitting data to remote server, a remote server for data collection, data analysis & monitoring generated by plurality of sensors and monitoring the process of disposal of sanitary waste remotely by sending alerts, messages, electronic emails etc. to user on his electronic device, are disclosed.

TABLE NO. 1

| Legend | Description |
| --- | --- |
| 1 | Opening lid |
| 2 | Hopper |
| 3 | Nozzle Sprayer |

TABLE NO. 1-continued

| Legend | Description |
| --- | --- |
| 4 | Shredder |
| 5 | Microcontroller |
| 6 | Mixing chamber |
| 7 | Cellulose Outlet Valve |
| 8 | Plastic Outlet Valve |
| 9 | Perforation sieve |
| 10 | Rotating Drum |
| 11 | Dryer |
| 12 | Shredder Motor |
| 13 | Display screen |
| 14 | Water Storage |
| 15 | Dilute Solution Storage |
| 16 | Concentrated Solution Storage |
| 17 | Concentrated solution input |
| 18 | Supporting Structure |
| 19 | Sewage outlet |
| 20 | Remote server |
| 21 | UV collection bin |
| 100 | Device for disposing sanitary waste |
| 101 | System for sanitary waste disposal |

DETAILED DESCRIPTION OF INVENTION

The present invention is described herein below with reference to the device and system for sanitary waste disposal; however, any description and drawings herein after should not be construed to limit the scope of present invention in any manner.

Present invention relates to a smart portable device and system for disposal of sanitary waste for disposing soiled/used sanitary pads, napkins, diapers, other feminine hygiene products etc. effectively and eco-friendly way by involving the steps like disintegration, disinfection, deodorization, decolorization, partial segregation & deactivation of super absorbent polymer which overcomes issues of smell, unhygienic environment & unsafe handling. The waste generated at the end is non-hazardous which is ready to put in normal waste channel and can be recycled. The novel system of disposal of used sanitary waste of present invention which helps in monitoring the operations of each component device at every stage from a remote location in real time monitoring to generate alerts etc.

Figure 1:
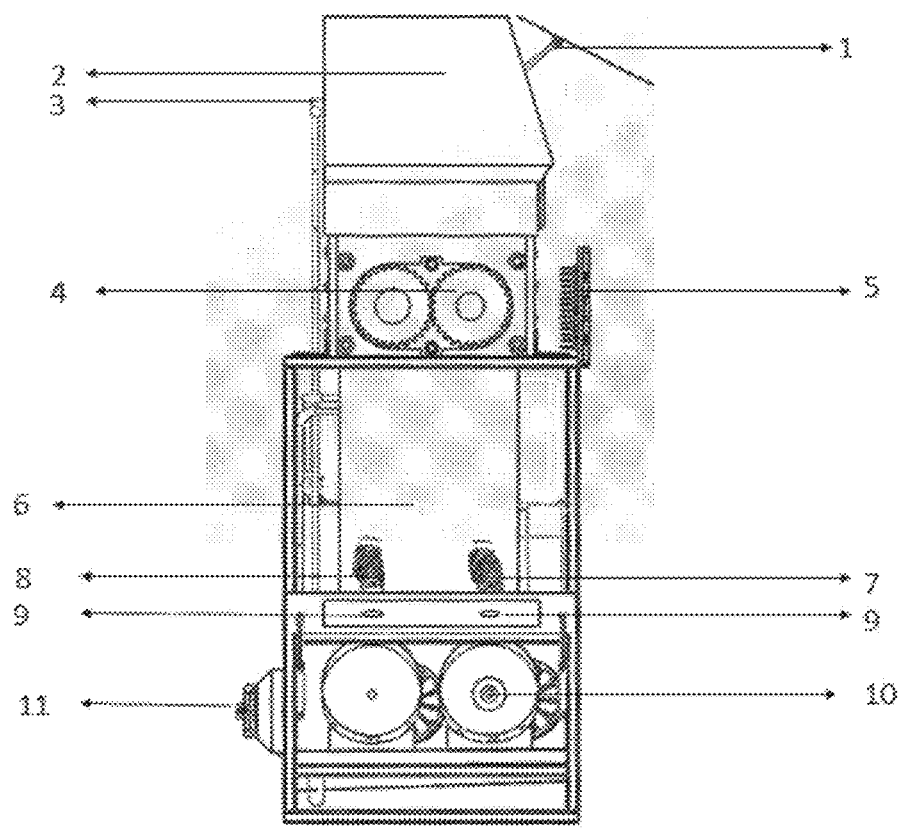
FIG. 1 cross sectional side view illustrates a smart, portable device for disposal of sanitary waste of present invention

Referring to FIG. 1, the cross sectional side view of the device for disposing sanitary waste in ecofriendly manner is shown.

As per FIG. 1, the invention relates to a smart portable device (100) for disposal of sanitary waste for disposing soiled/used sanitary pads, napkins diapers and other feminine hygiene products effectively and eco-friendly, wherein a device may comprises a supporting structure frame (18) on which all the other components of the device arc mounted, an opening lid (1) for loading the sanitary waste, hingely connected to a hopper (2) with a guiding arrangement wherein; said hopper (2) may receive and guide soiled sanitary waste to the shredder (4) and further comprises at least two spray nozzles (3) for spraying the dilute disinfectant solution and water on the soiled sanitary waste pumped from a dilute solution storage (15) and water storage (14) respectively, a shredder (4) connected to said hopper (2) by nut and bolt arrangement is operably coupled to a motor (12) for shredding the sanitary pads/diapers by rotating the shredder blades clockwise as well as anticlockwise for predetermined time duration, a mixing chamber (6) wherein the shredded sanitary waste is collected and incubated for homogenously mixing with water added via water pump for a predetermined time, at least two separate rotating drum (10) for rotating and dewatering the semisolid waste collected in it, a dryer (11) for drying the wet cellulose and plastic in rotating drums (10) by blowing hot air and an outlet (19) to discharge water separated out from the device into municipal sewage line.

In an embodiment, a smart portable device for disposal of sanitary waste for disposing soiled/used sanitary pads, napkins diapers or other feminine hygiene products effectively and eco-friendly, wherein; said opening lid (1) may operate automatically with a proximity sensor to open when a user comes in contact with the lid (1) and a motion sensor for sending real time data regarding motion of hopper (2) and other devices to remote server (20).

Said spray nozzles (3) wherein one is operatively coupled to a dilute disinfection solution pump to pump the solution from dilute solution storage (15) by receiving signal from microcontroller (5) and another to a water storage (14) wherein water is pumped and sprayed via nozzle (3) simultaneously with said disinfectant solution.

In another embodiment said shredder (4) further comprises of shredder blades to rotate clockwise and anticlockwise for a predetermined time by a motor (12) which in turn operatively coupled to the microcontroller (5) to complete the predetermined rotations.

Said predetermined time for rotating motor (12) by a microcontroller (5) is 3 to 5 minutes/cycle of at least 30 items and may vary depending upon number of items to be treated per cycle.

In one embodiment, a smart portable device for disposal of sanitary waste for disposing soiled/used sanitary pads, napkins diapers or other feminine hygiene products effectively and eco-friendly, wherein in the said mixing chamber (6) water is added by water pump for preparing a homogenous solution of shredded sanitary waste and incubated for 3-15 min/cycle of at least 30 items to obtain a decolorized, deodorized, disinfected and deactivated SAP (Super Absorbent Polymer) sanitary waste to separate cellulose and plastic.

Said mixing chamber (6) may operatively couple to a motor in order to rotate clockwise and anticlockwise and thus separates the cellulose and plastic through the perforation sieve (9) at the bottom portion of said mixing chamber (6) and pretreated, disinfected and neutral water may drain off through the outlet (19) into municipal sewage line.

Said mixing chamber (6) further comprises, at least two automatic valves wherein one of the valves comprises mesh to separate cellulose and operated by an On/Off signal from microcontroller (5) and another for separation of plastic respectively as per their density difference.

In an embodiment said predetermined time for homogenously mixing the sanitary waste in said mixing chamber (6) is ranging between 5-20 minutes/cycle.

In yet another embodiment of present invention, a smart portable device for disposal of sanitary waste for disposing soiled/used sanitary pads, napkins, diapers or other feminine hygiene products effectively and eco-friendly, wherein said two separate rotating drums (10) for cellulose and plastic respectively for separating solution, water and drying of solid output received from mixing chamber (6) by rotating the said drums at a speed of 10-100 rpm to drain out liquid through mesh as a part of rotating drum and get the dried, decolorized, deodorized, disintegrated, disinfected cellulose and plastic. A dryer (11) means for blowing hot air and removing the water content of solid material.

The dried byproducts obtain through a complete disposal cycle of sanitary waste may recycled and used in making packaging material or fuel by creating burning pallets out of it.

Said disinfectant solution may store in concentrated disinfectant solution storage (16) is an organic or an inorganic disinfectant capable of disinfecting the sanitary waste effectively pumped to dilute solution storage (15) for mixing with water received from said water storage (14) in the ratio ranging from 1:1 to 1:20. The amount of said disinfectant solution required for disinfecting the sanitary waste is in the range of 50-200 ml/item of sanitary waste.

In one embodiment, a smart portable device for disposal of sanitary waste for disposing soiled/used sanitary pads, napkins diapers or other feminine hygienic products effectively and eco-friendly, wherein said device (100) may further comprises a concentrated disinfection solution input (17) for breaking the chemical/disinfectant bottle seal, a pump for pumping the disinfection solution to spray nozzle (3) wherein; said disinfection solution is sprayed on the pads simultaneously with shredding.

Figure 2:
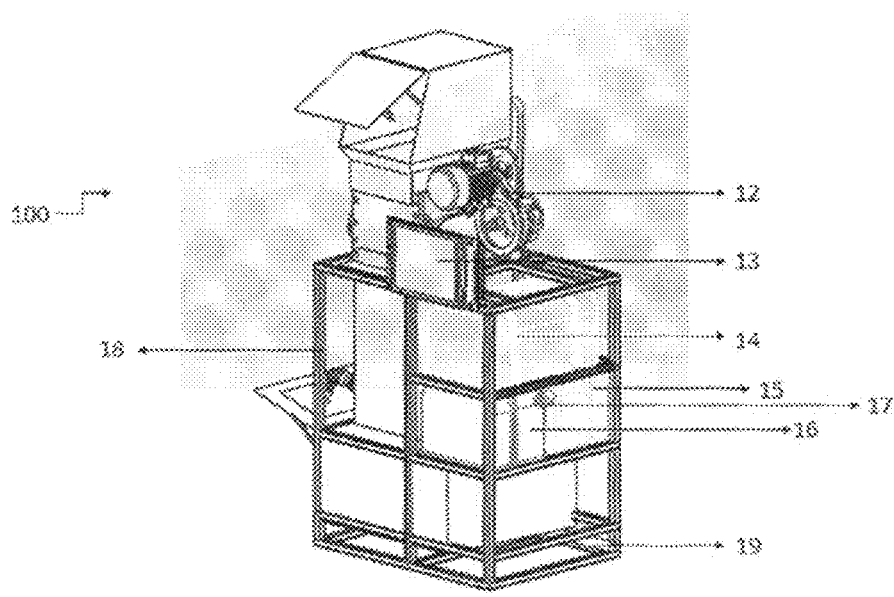
FIG. 2 illustrates isometric view of a smart, portable device for disposal of sanitary waste of present invention

Referring to FIG. 2, an isometric view of the device for disposal of sanitary waste such as sanitary pads, diapers or other feminine hygiene products is shown.

In an exemplary embodiment, in an event wherein said dilute solution storage (15) is emptied as indicated by a level sensor, a water storage container (14) wherein water may mixed with a dilute disinfectant solution storage (15) with an automated valve operatively coupled to said microcontroller (5) and a concentrated disinfectant solution storage (16) wherein concentrated solution may pumped to a dilute disinfectant solution storage (15) via automatically operated pump and thus the dilute disinfectant solution storage (15) filled up again my mixing the concentrated solution as well as water automatically depending upon disposal capacity of a device (100).

In other embodiment of the present invention, all the storages (14, 15, 16) may further comprises level sensors to detect the level of the liquid in respective storage container, transmit the data to the remote server (20) and monitor the operations of valve and pump to fill up said dilute disinfectant solution storage (15) automatically.

In another embodiment, after completing one cycle of processing sanitary waste in the device (100), a washing cycle is run with water pumped from water storage (14) to one of the spray nozzle (3) in order to spray water to clean hopper, shredder and other components of device (100) as a blank cycle.

The method for disposal of sanitary waste for disposing soiled/used sanitary pads, diapers and other feminine hygiene products napkins effectively and eco-friendly by using a device as mentioned herein above, wherein said method may comprise a cleaning cycle after every 10-50 items disposal cycle.

Figure 3:
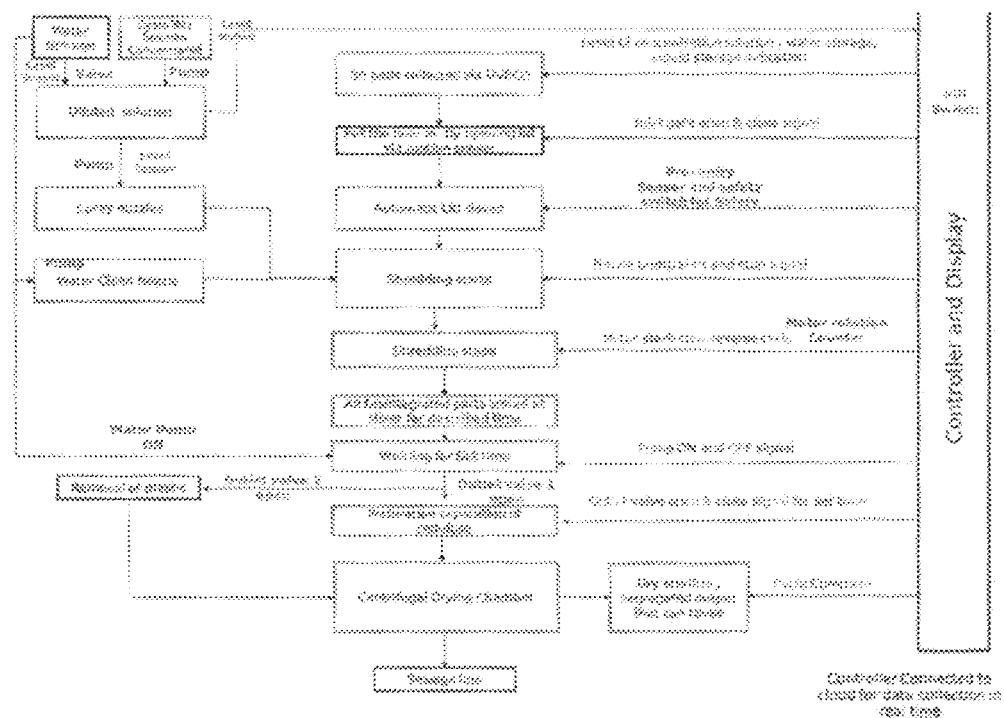
FIG. 3 illustrates the flow diagram of method of disposing sanitary waste by using device of present invention

FIG. 3 relates to a method of disposing sanitary waste in effectively and eco-friendly way by using a device (100) as mentioned herein above, wherein said method comprising steps of; opening the lid of UV collection bin (21) for the user to throw the used sanitary pads diapers or other feminine hygiene products inside, storing the used pads and treating the same with ultraviolet rays in order to inactivate the microorganisms preset on the surface of used sanitary waste, sending an alert to operator at remote location when the UV collection bin (21) is full of capacity, collecting the pretreated sanitary waste from said UV collection bins (21) by the operator, unloading the said pretreated sanitary waste into sanitary waste disposal device (100) by opening of the lid (1) when the operator comes in proximity of disposal device (100), closing the lid (1) after putting the soiled waste in hopper (2), pushing the sanitary waste to shredder (4) wherein shredding cycle starts so as to shred the waste into small pieces for a predetermined time period, spraying the dilute disinfectant solution via spray nozzle (3) pumped from the dilute solution storage (15) during the shredding process for disinfecting soiled and shredded sanitary waste, stopping the spraying of disinfectant after a predetermined period by switching off the pump by microcontroller (5), pushing the shredded waste into mixing chamber (6) in order to homogenize the waste by adding water, mixing & whirling the solution in said mixing chamber (6), perforating the solution through sieves (9), collecting the semisolid cellulose and plastic waste into two separate rotating drums (10), drying and separating cellulose and plastic ready for recycling and draining out the neutral liquid into municipal sewage line.

In an embodiment of present invention, the method of disposing sanitary waste may monitored remotely by a remote server (20) by receiving sensor data and the remote server (20) may send alerts, sms or any other audio visual signals for operator regarding action required.

The main component of sanitary pads, napkins, diapers is super absorbent polymer (SAP) is a material having properties to absorbed the water body multiple times of its own weight. To do complete disinfection of sanitary waste the deactivation and deswelling of sanitary napkin is a mandatory process. Present invention provides an efficient deactivation and deswelling of super absorbent polymer using PH difference as reverse osmosis (RO). PH of disinfectant solution used in present process is having difference in terms of PH as compared to PH of super absorbent polymer (SAP) of used pad/diaper. Because of RO the external environment presses the SAP & deswelling happens.

In an embodiment wherein the time required for completing one cycle of disposing sanitary waste is in the range of 10-30 minutes/cycle for at least 30 items capacity.

Figure 4:
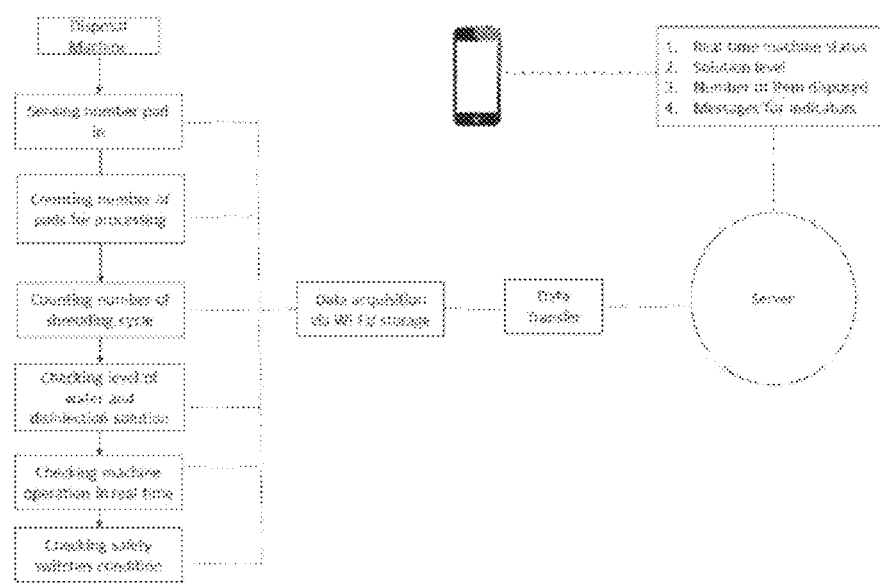
FIG. 4 illustrates the flow diagram of smart system of sanitary waste disposal.

FIG. 4 relates to a system (101) for effectively monitoring and disposing sanitary waste in an eco-friendly manner.

The system for disposing sanitary waste and monitoring the disposing cycle in an eco-friendly way comprising; a plurality of UV collection bins (21) mounted at remote locations for collecting the soiled/used sanitary pads. diapers and other feminine hygienic products for treating the waste by ultraviolet rays to inactivate the microorganisms present on surface of used waste, a sanitary waste disposal device (100) at a centralized location wherein; each device (100) may comprises a supporting structure frame (18) on which all the other components of the device are mounted, an opening lid (1) for loading the sanitary waste, hingely connected to a hopper (2) with a guiding arrangement wherein; said hopper (2) may receive and push soiled sanitary waste to the shredder (4) and further comprises at least two spray nozzles (3) for spraying the dilute disinfectant solution on the soiled sanitary waste pumped from a dilute disinfectant solution storage (15) and water from water storage (14), a shredder (4) connected to said hopper (2) by nut and bolt arrangement is operably coupled to a controlled motor (12) for shredding the sanitary waste items by rotating the shredder blades clockwise as well as anticlockwise for a cycle for predetermined time duration, a mixing chamber (6) for homogenously mixing shredded sanitary waste with water added via water pump for a predetermined time, at least two separate rotating drums (10) for rotating and drying the semisolid waste collected in it, a dryer (11) for drying the wet cellulose and plastic in rotating drums (10) by blowing hot air and an outlet (19) at the lowermost portion of said mixing chamber (6) to discharge water separated out from the device into municipal sewage line, a plurality of sensors for acquiring data and sending to a remote server (20), at least three automatic valves, a remote server (20) for data analyzing, data managing and system monitoring, a data transmission module, a microcontroller (5) for sending signals for opening or closing of valves, pumps, monitoring rotations of motor etc, a display screen (13) for displaying a status of stages of disposal and an electronic device for receiving alerts or messages or electronic mails received by an operating person.

In one embodiment said UV collection bins (21) may be mounted at washrooms or the like places for collecting the sanitary waste thrown by user.

In an exemplary embodiment, a system for disposal of sanitary waste for disposing soiled/used sanitary pads, napkins, diapers or other feminine hygiene products effectively and eco-friendly, wherein said plurality of sensors means for detecting various parameters involved in the process of disposal selected from but not limited to level sensor for determining the level of disinfectant solution in concentrated solution storage (16), water storage (14), dilute solution storage (15), proximity sensor for opening the lid (1) when the user comes in proximity of device, limit sensor for indicating the collection bin (21) capacity, motor (12) rotation measurement sensor or any combination thereof.

In an embodiment, system for disposal of sanitary waste for disposing soiled/used sanitary pads, napkin, diapers and other feminine hygiene products effectively and eco-friendly, wherein said system may further comprises of outlet valves, HMI (Human Machine Interface) display module for displaying the stage of disposing method of present invention.

In an embodiment, a system for disposal of sanitary waste for disposing soiled/used sanitary pads, diapers and other feminine hygiene products effectively and eco-friendly, wherein said data transmission module is either wired or wireless network.

In an embodiment, a system for disposal of sanitary waste for disposing soiled/used sanitary pads, napkins, diapers and other feminine hygiene products effectively and eco-friendly, wherein said remote server (20) may comprise a physical server or a cloud server located at the central station and operated by human expert.

In yet another embodiment of the present invention, a system for disposal of sanitary waste for disposing soiled/used sanitary pads or napkins, diapers and other feminine hygiene products effectively and eco-friendly, wherein system may comprise alerts to be sent by sms or electronic mail in case of any liquid refill action is needed, bin capacity full indication, cycle complete alert or any non-functioning of the system.

The smart, portable device for disposal of sanitary waste of present invention provides an alternative to sanitary waste disposal management in environment friendly way. Also, present system provides a real time monitoring of each such device and thus provides a complete solution to the problem of sanitary waste disposal.

The invention provides, a safe, environment friendly, clean, easy way to dispose sanitary waste without polluting atmosphere wherein, the sanitary waste can be disintegrate, deodorized, decolorized, disinfect and deactivation of SAP in an efficient manner. The by products such as cellulose and plastic can be recycled and used in packing etc. The disposal method provides three fold disinfection wherein; first the waste is treated with ultra violet rays to stop growth of microorganisms, the second stage provides shredding into small pieces for easy mixing with disinfectant and treatment with disinfectant provides complete disinfection of sanitary waste to achieve deodorization, decolorization and disposal.

In one embodiment of the present invention disinfection of sanitary pads is achieved in the ratio 98 to 99.999%.

Following table illustrates the effectiveness and efficiency of a system and device for disposal of sanitary waste disclosed by present invention.

| Sr. No. | Trial | Result | Method |
|---|---|---|---|
| 1 | Disinfection trial | Complete disinfection | Standard plate count |
| 2 | Decolorization trial | Partial Decolorization of the Sanitary napkin | Visual Examination |
| 3 | pH | 5 | — |
| 4 | Chemical Oxygen demand | 1280.49 mg/Lit | IS: 3025 Part- 58 (R.A: 2006) |
| 5 | Biological Oxygen demand | 190 mg/Lit | IS: 3025 Part- 44 (R.A: 2003) |
| 6 | Disinfection trial | <2 | IS: 1622 (R.A: 2014) |

The advantages of present invention are;
Smart, portable device, can be monitored remotely
Affordable
Environment friendly
The waste material obtained at the end of cycle can be recycled
Very short processing time
95% material recovery
Safe, easy to handle

I claim:

1. A hygienic disposal device of sanitary waste comprising:
    a supporting structure frame for mounting one or more components of the hygienic disposal device;
    an opening lid for loading the sanitary waste, the opening lid hingedly connected to a hopper with a guiding arrangement, wherein the hopper is adapted to receive soiled sanitary waste and further comprises at least two spray nozzles for spraying dilute disinfectant solution on the soiled sanitary waste from one nozzle of the at least two spray nozzles and water from another nozzle of the at least two spray nozzles;
    a shredder connected to the hopper by a nut and bolt arrangement, wherein the shredder is operably coupled to a shredder motor for shredding the soiled sanitary waste guided by said hopper for a predetermined time duration;
    a mixing chamber arranged below the shredder for homogenously mixing, whirling and spinning shredded and disinfected sanitary waste with water added via a water pump from water storage for a predetermined time;
    at least two valves positioned at a bottom of the mixing chamber for separating cellulose and plastic in the soiled sanitary waste, wherein one valve of the at least two valves comprises mesh situated at a bottom portion of the one valve to separate the cellulose and another valve of the at least two valves separates the plastic and other waste material of the soiled sanitary waste into a rotating drum chamber;
    at least two separate rotating drums mounted at a lowermost portion of the supporting structure frame for receiving semisolid cellulose and semisolid plastic waste from the mixing chamber for dewatering and drying; and
    a dryer for drying the semisolid cellulose and the semisolid plastic in the at least two separate rotating drums by blowing hot air and an outlet arranged at a lower portion of mixing chamber to discharge water separated out from the hygienic disposal device into a municipal sewage line.

2. The hygienic disposal device of claim 1, wherein the dilute disinfectant solution is sprayed by the one nozzle after being pumped from a dilute disinfection solution storage where the dilute disinfectant solution is stored simultaneously with a shredding process by the shredder.

3. The hygienic disposal device of claim 1, wherein the dilute disinfectant solution is organic or inorganic disinfectant or a combination thereof stored at concentrated solution storage and pumped to dilute solution storage for mixing with the water received from the water storage in a ratio ranging from 1:1 to 1:20.

4. The hygienic disposal device of claim 1, wherein an amount of the dilute disinfectant solution required for disinfecting the soiled sanitary waste is in a range of 50-200 mL/item of the soiled sanitary waste.

5. A system for sanitary waste disposal comprising:
    a plurality of ultraviolet (UV) collection bins mounted at remote locations for collecting soiled sanitary waste and treating the soiled sanitary waste by ultraviolet rays during storage in the plurality of UV collection bin to inactivate microorganisms present on a surface of the soiled sanitary waste;
    a hygienic disposal device at a centralized location, wherein the hygienic disposal device comprises a supporting structure frame on which one or more components of the hygienic disposal device are mounted;
    an opening lid for loading the sanitary waste, hingedly connected to a hopper with a guiding arrangement, wherein the hopper is configured to receive and push the soiled sanitary waste to a shredder and the shredder comprises at least two spray nozzles for spraying dilute disinfectant solution on the soiled sanitary waste pumped from a dilute disinfectant solution storage and spray water pumped from water storage, the shredder connected to the hopper by a nut and bolt arrangement and the shredder operably coupled to a controlled motor for shredding the soiled sanitary waste by rotating blades of the shredder clockwise as well as anti-clockwise for a cycle for a predetermined time duration;
    a mixing chamber arranged below the shredder for homogenously mixing, whirling and spinning shredded and disinfected sanitary waste with water added via a water pump from the water storage for a predetermined time;
    at least two valves positioned at a bottom of the mixing chamber for separating cellulose and plastic in the soiled sanitary waste, wherein at least one valve of the at least two valves comprises mesh situated at a bottom portion of the at least one valve to separate the cellulose and another valve of the at least one valve to separate the plastic and other waste material of the soiled sanitary waste into;
    at least two separate rotating drums mounted at a lowermost portion of the supporting structure frame for receiving semisolid cellulose and semisolid plastic waste from the mixing chamber for dewatering and drying;

a dryer for drying the semisolid cellulose and the semisolid plastic in the at least two separate rotating drums by blowing hot air and an outlet arranged at a lower portion of mixing chamber to discharge water separated out from the hygienic disposal device into a municipal sewage line; and a plurality of sensors for acquiring data and sending to a remote server, at least three automatic valves, the remote server for data analyzing, data managing and system monitoring, a data transmission module, a microcontroller for controlling automatic operations of the one or more components, a display screen for displaying a status of stages of disposal and an electronic device for receiving alerts or messages or electronic mails received by an operating person.

6. The system of claim 5, wherein the microcontroller is configured to receive real time data from the remote server for controlling operations of opening or closing of the at least three automatic valves, the water pump, and rotations of the controlled motor.

7. The system of claim 5, wherein the remote server is either a physical server or cloud based server configured to receive real time data from the plurality of sensors wirelessly, analyze, monitor disposal process steps and send an action required to the operating person by the alerts, the messages, the electronic mails or any other communication means.

8. A method of disposing sanitary waste using the hygienic disposal device of claim 1, wherein the method comprises the steps of:

opening a lid of an ultraviolet (UV) collection bin (21) for a user to throw the soiled sanitary waste inside for storing and treating the soiled sanitary waste with ultraviolet rays in order to inactivate microorganisms preset on a surface of the soiled sanitary waste to yield pretreated sanitary waste;

sending an alert to an operator at a remote location when the UV collection bin is at full of capacity;

collecting the pretreated sanitary waste from the UV collection bins by the operator;

unloading the pretreated sanitary waste into the hygienic disposal device by opening of the opening lid when the operator comes in proximity to the hygienic disposal device;

closing the opening lid after putting the pretreated sanitary waste in the hopper, guiding the pretreated sanitary waste to the shredder, wherein a shredding cycle starts so as to shred the pretreated sanitary waste into small pieces for the predetermined time duration;

spraying the dilute disinfectant solution via the one nozzle pumped from dilute solution storage during the shredding cycle for disinfecting the pretreated sanitary to yield shredded waste waste;

stopping the spraying of the dilute disinfectant solution after a predetermined period by switching off a pump by a microcontroller;

pushing the shredded waste into the mixing chamber in order to homogenize the shredded waste by adding the water, mixing, whirling and rotating a solution of the water and the dilute disinfectant solution in the mixing chamber for the predetermined time;

perforating the solution through sieves;

collecting the semisolid cellulose and semisolid plastic waste into the at least two separate rotating drums for drying and separating the semisolid cellulose and the semisolid plastic ready for recycling and draining out neutral liquid into the municipal sewage line; and running a cleaning cycle throughout the hygienic disposal device by spraying the water pumped from the water storage through the another nozzle positioned in the hopper.

9. The method of claim 8, wherein the predetermined time for homogenously mixing the sanitary waste in the mixing chamber ranges between 5-20 minutes/cycle.

10. The method of claim 8, wherein an amount of time required for completing one cycle of disposing the soiled sanitary waste is in a range of 10-30 minutes/cycle for at least 30 item capacity.

* * * * *